US007070798B1

(12) United States Patent
Michal et al.

(10) Patent No.: US 7,070,798 B1
(45) Date of Patent: *Jul. 4, 2006

(54) COATINGS FOR IMPLANTABLE MEDICAL DEVICES INCORPORATING CHEMICALLY-BOUND POLYMERS AND OLIGOMERS OF L-ARGININE

(75) Inventors: Eugene T Michal, San Francisco, CA (US); Syed F A Hossainy, Fremont, CA (US); Paul M Consigny, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 313 days.

This patent is subject to a terminal disclaimer.

(21) Appl. No.: 10/177,156

(22) Filed: Jun. 21, 2002

(51) Int. Cl.
*A61F 2/02* (2006.01)
*A61K 9/14* (2006.01)
(52) U.S. Cl. .................. 424/423; 424/484; 424/486
(58) Field of Classification Search ............... 424/423, 424/484, 486
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,835,175 A | 9/1974 | Carpino et al. | 260/463 |
| 3,849,514 A | 11/1974 | Gray, Jr. et al. | 260/857 |
| 4,226,243 A | 10/1980 | Shalaby et al. | 128/335.5 |
| 4,329,383 A | 5/1982 | Joh | 428/36 |
| 4,343,931 A | 8/1982 | Barrows | 528/291 |
| 4,529,792 A | 7/1985 | Barrows | 528/291 |
| 4,611,051 A | 9/1986 | Hayes et al. | 528/295.3 |
| 4,656,242 A | 4/1987 | Swan et al. | 528/295.3 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,908,404 A | 3/1990 | Benedict et al. | 525/54.11 |
| 4,917,309 A | 4/1990 | Zander et al. | 241/5 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,025,001 A | 6/1991 | Loscalzo et al. | 514/91 |
| 5,100,992 A | 3/1992 | Cohn et al. | 424/501 |
| 5,112,457 A | 5/1992 | Marchant | 204/165 |
| 5,133,742 A | 7/1992 | Pinchuk | 623/1 |
| 5,155,137 A | 10/1992 | Keefer et al. | 514/611 |
| 5,163,952 A | 11/1992 | Froix | 623/1 |
| 5,165,919 A | 11/1992 | Sasaki et al. | 424/488 |
| 5,187,183 A | 2/1993 | Loscalzo et al. | 514/400 |
| 5,202,129 A | 4/1993 | Samejima et al. | 424/489 |
| 5,219,980 A | 6/1993 | Swidler | 528/272 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,356,890 A | 10/1994 | Loscalzo et al. | 514/210 |
| 5,366,997 A | 11/1994 | Keefer et al. | 614/611 |
| 5,380,299 A | 1/1995 | Fearnot et al. | 604/265 |
| 5,405,919 A | 4/1995 | Keefer et al. | 525/377 |
| 5,417,981 A | 5/1995 | Endo et al. | 424/486 |
| 5,424,077 A | 6/1995 | Lajoie | 424/641 |
| 5,428,070 A | 6/1995 | Cooke et al. | 514/557 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,482,720 A | 1/1996 | Murphy et al. | 424/489 |
| 5,485,496 A | 1/1996 | Lee et al. | 378/64 |
| 5,516,881 A | 5/1996 | Lee et al. | 528/320 |
| 5,536,723 A | 7/1996 | Loscalzo et al. | 514/247 |
| 5,543,099 A | 8/1996 | Zhang et al. | 264/115 |
| 5,569,463 A | 10/1996 | Helmus et al. | 424/426 |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |

(Continued)

FOREIGN PATENT DOCUMENTS

DE 42 24 401 1/1994

(Continued)

OTHER PUBLICATIONS

U.S. Appl. No. 10/176,499, filed Jun. 21, 2002, Hossainy et al.

(Continued)

*Primary Examiner*—Carlos A. Azpuru
(74) *Attorney, Agent, or Firm*—Squire, Sanders & Dempsey L.L.P.

(57) ABSTRACT

A coating for an implantable medical device is disclosed. The coating comprises a polymer and an amino acid chemically bonded, attached or conjugated to the polymer. In one embodiment, the coating can include a therapeutic substance. In lieu of bonding the amino acid to the polymer, the amino acid can be chemically bonded to the therapeutic substance or both the substance and the polymer. The amino acid can be polymers and/or oligomers of L-arginine, and copolymers of L-arginine with lysine. The coating can optionally include a nitric oxide donor, such as diazenium diolate type nitric oxide donors, chemically conjugated to the amino acid.

26 Claims, No Drawings

U.S. PATENT DOCUMENTS

| | | | |
|---|---|---|---|
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,639,441 A | 6/1997 | Sievers et al. | 424/9.3 |
| 5,644,020 A | 7/1997 | Timmermann et al. | 528/288 |
| 5,649,977 A | 7/1997 | Campbell | 623/1 |
| 5,650,442 A | 7/1997 | Mitchell et al. | 514/611 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,804,318 A | 9/1998 | Pinchuk et al. | 428/421 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,852,058 A | 12/1998 | Cooke et al. | 514/564 |
| 5,854,376 A | 12/1998 | Higashi | 528/288 |
| 5,858,746 A | 1/1999 | Hubbell et al. | 435/177 |
| 5,861,168 A * | 1/1999 | Cooke et al. | 424/424 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,874,165 A | 2/1999 | Drumheller | 428/308.4 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,891,459 A | 4/1999 | Cooke et al. | 424/424 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,945,452 A | 8/1999 | Cooke et al. | 514/564 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,060,534 A | 5/2000 | Ronan et al. | 523/113 |
| 6,063,432 A | 5/2000 | Maxwell et al. | 426/656 |
| 6,077,543 A | 6/2000 | Gordon et al. | 424/489 |
| 6,080,488 A | 6/2000 | Hostettler et al. | 428/423.3 |
| 6,095,134 A | 8/2000 | Sievers et al. | 128/200.14 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,117,872 A | 9/2000 | Maxwell et al. | 514/249 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,183,783 B1 | 2/2001 | Benoit et al. | 424/497 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,228,346 B1 | 5/2001 | Zhang et al. | 424/45 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,166 B1 | 10/2001 | Barry et al. | 623/1.46 |
| 6,306,176 B1 | 10/2001 | Whitbourne | 623/23.59 |
| 6,306,993 B1 | 10/2001 | Rothbard et al. | 526/304 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B1 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B1 | 11/2002 | Spada et al. | 514/311 |
| 6,494,862 B1 | 12/2002 | Ray et al. | 604/96.01 |
| 6,503,538 B1 | 1/2003 | Chu et al. | 424/497 |
| 6,503,556 B1 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | 251/252.1 |
| 6,527,801 B1 | 3/2003 | Dutta | 623/1.46 |

| | | | |
|---|---|---|---|
| 6,527,863 B1 | 3/2003 | Pacetti et al. ............... 118/500 |
| 6,528,526 B1 | 3/2003 | Myers et al. ............... 214/311 |
| 6,530,950 B1 | 3/2003 | Alvarado et al. .......... 623/1.13 |
| 6,530,951 B1 | 3/2003 | Bates et al. ................ 623/1.45 |
| 6,540,776 B1 | 4/2003 | Sanders Millare et al. 623/1.15 |
| 6,544,223 B1 | 4/2003 | Kokish ................. 604/103.01 |
| 6,544,543 B1 | 4/2003 | Mandrusov et al. ........ 424/422 |
| 6,544,582 B1 | 4/2003 | Yoe ........................... 427/2.24 |
| 6,555,157 B1 | 4/2003 | Hossainy .................. 427/2.24 |
| 6,558,733 B1 | 5/2003 | Hossainy et al. .......... 427/2.24 |
| 6,565,659 B1 | 5/2003 | Pacetti et al. .............. 118/500 |
| 6,572,644 B1 | 6/2003 | Moein ...................... 623/1.11 |
| 6,585,755 B1 | 7/2003 | Jackson et al. ............ 623/1.15 |
| 6,585,765 B1 | 7/2003 | Hossainy et al. .......... 623/1.45 |
| 6,585,926 B1 | 7/2003 | Mirzaee ..................... 264/400 |
| 6,605,154 B1 | 8/2003 | Villareal .................... 118/500 |
| 6,616,765 B1 | 9/2003 | Hossaony et al. ......... 623/1.45 |
| 6,623,448 B1 | 9/2003 | Slater ..................... 604/95.01 |
| 6,625,486 B1 | 9/2003 | Lundkvist et al. ............ 604/21 |
| 6,645,135 B1 | 11/2003 | Bhat ............................. 600/3 |
| 6,645,195 B1 | 11/2003 | Bhat et al. .................. 604/528 |
| 6,656,216 B1 | 12/2003 | Hossainy et al. .......... 623/1.13 |
| 6,656,506 B1 | 12/2003 | Wu et al. .................... 424/489 |
| 6,660,034 B1 | 12/2003 | Mandrusov et al. ....... 623/1.42 |
| 6,663,662 B1 | 12/2003 | Pacetti et al. ............. 623/1.13 |
| 6,663,880 B1 | 12/2003 | Roorda et al. .............. 424/423 |
| 6,666,880 B1 | 12/2003 | Chiu et al. ................. 623/1.11 |
| 6,673,154 B1 | 1/2004 | Pacetti et al. .............. 118/500 |
| 6,673,385 B1 | 1/2004 | Ding et al. ................ 427/2.28 |
| 6,689,099 B1 | 2/2004 | Mirzaee ..................... 604/107 |
| 6,695,920 B1 | 2/2004 | Pacetti et al. .............. 118/500 |
| 6,706,013 B1 | 3/2004 | Bhat et al. ............... 604/96.01 |
| 6,709,514 B1 | 3/2004 | Hossainy ..................... 118/52 |
| 6,712,845 B1 | 3/2004 | Hossainy .................. 623/1.42 |
| 6,713,119 B1 | 3/2004 | Hossainy et al. .......... 427/2.25 |
| 6,716,444 B1 | 4/2004 | Castro et al. ............... 424/422 |
| 6,723,120 B1 | 4/2004 | Yan ........................... 623/1.15 |
| 6,733,768 B1 | 5/2004 | Hossainy et al. ........... 424/426 |
| 6,740,040 B1 | 5/2004 | Mandrusov et al. ........ 600/439 |
| 6,743,462 B1 | 6/2004 | Pacetti ...................... 427/2.24 |
| 6,746,481 B1 | 6/2004 | Larik et al. |
| 6,749,626 B1 | 6/2004 | Bhat et al. ................... 623/1.1 |
| 6,753,071 B1 | 6/2004 | Pacetti ....................... 428/212 |
| 6,758,859 B1 | 7/2004 | Dang et al. ................ 623/1.15 |
| 6,759,054 B1 | 7/2004 | Chen et al. ................. 424/423 |
| 6,764,505 B1 | 7/2004 | Hossainy et al. .......... 623/1.15 |
| 2001/0007083 A1 | 7/2001 | Roorda ...................... 623/1.15 |
| 2001/0014717 A1 | 8/2001 | Hossainy et al. ............. 525/60 |
| 2001/0018469 A1 | 8/2001 | Chen et al. ................. 523/121 |
| 2001/0020011 A1 | 9/2001 | Mathiowitz et al. .......... 514/44 |
| 2001/0029351 A1 | 10/2001 | Falotico et al. ......... 604/103.02 |
| 2001/0037145 A1 | 11/2001 | Guruwaiya et al. ........ 623/1.15 |
| 2001/0051608 A1 | 12/2001 | Mathiowitz et al. .......... 514/44 |
| 2002/0005206 A1 | 1/2002 | Falotico et al. ............. 128/898 |
| 2002/0007213 A1 | 1/2002 | Falotico et al. ............. 623/1.21 |
| 2002/0007214 A1 | 1/2002 | Falotico ..................... 623/1.21 |
| 2002/0007215 A1 | 1/2002 | Falotico et al. ............. 623/1.21 |
| 2002/0009604 A1 | 1/2002 | Zamora et al. .............. 428/450 |
| 2002/0016625 A1 | 2/2002 | Falotico et al. ............. 623/1.13 |
| 2002/0032414 A1 | 3/2002 | Ragheb et al. .............. 604/265 |
| 2002/0032434 A1 | 3/2002 | Chudzik et al. ......... 604/890.1 |
| 2002/0051730 A1 | 5/2002 | Bodnar et al. ................ 422/33 |
| 2002/0071822 A1 | 6/2002 | Uhrich .................... 424/78.37 |
| 2002/0077693 A1 | 6/2002 | Barclay et al. ............. 623/1.13 |
| 2002/0082679 A1 | 6/2002 | Sirhan et al. ............... 623/1.15 |
| 2002/0087123 A1 | 7/2002 | Hossainy et al. ........... 604/198 |
| 2002/0091433 A1 | 7/2002 | Ding et al. .................. 623/1.2 |
| 2002/0094440 A1 | 7/2002 | Llanos et al. ............... 428/421 |
| 2002/0111590 A1 | 8/2002 | Davila et al. ............... 604/265 |
| 2002/0120326 A1 | 8/2002 | Michal ...................... 623/1.15 |
| 2002/0123801 A1 | 9/2002 | Pacetti et al. ............. 623/1.46 |
| 2002/0142039 A1 | 10/2002 | Claude ....................... 424/486 |
| 2002/0155212 A1 | 10/2002 | Hossainy ................... 427/2.25 |
| 2002/0165608 A1 | 11/2002 | Llanos et al. ............... 623/1.45 |
| 2002/0176849 A1 | 11/2002 | Slepian ..................... 424/93.7 |
| 2002/0183581 A1 | 12/2002 | Yoe et al. ....................... 600/3 |
| 2002/0188037 A1 | 12/2002 | Chudzik et al. ............ 523/112 |
| 2002/0188277 A1 | 12/2002 | Roorda et al. .............. 604/523 |
| 2003/0004141 A1 | 1/2003 | Brown ........................ 514/152 |
| 2003/0028243 A1 | 2/2003 | Bates et al. ................ 623/1.15 |
| 2003/0028244 A1 | 2/2003 | Bates et al. ................ 623/1.15 |
| 2003/0031780 A1 | 2/2003 | Chudzik et al. ............. 427/2.1 |
| 2003/0032767 A1 | 2/2003 | Tada et al. .................. 528/310 |
| 2003/0036794 A1 | 2/2003 | Ragheb et al. ............. 623/1.15 |
| 2003/0039689 A1 | 2/2003 | Chen et al. ................. 424/468 |
| 2003/0040712 A1 | 2/2003 | Ray et al. ................... 604/173 |
| 2003/0040790 A1 | 2/2003 | Furst ......................... 623/1.11 |
| 2003/0059520 A1 | 3/2003 | Chen et al. .................. 427/2.1 |
| 2003/0060877 A1 | 3/2003 | Falotico et al. ............ 623/1.42 |
| 2003/0065377 A1 | 4/2003 | Davila et al. ............... 623/1.13 |
| 2003/0072868 A1 | 4/2003 | Harish et al. .............. 427/2.24 |
| 2003/0073961 A1 | 4/2003 | Happ ......................... 604/274 |
| 2003/0083646 A1 | 5/2003 | Sirhan et al. ............. 604/891.1 |
| 2003/0083739 A1 | 5/2003 | Cafferata ................... 623/1.42 |
| 2003/0097088 A1 | 5/2003 | Pacetti .......................... 604/19 |
| 2003/0097173 A1 | 5/2003 | Dutta ......................... 623/1.38 |
| 2003/0099712 A1 | 5/2003 | Jayaraman ................. 424/486 |
| 2003/0105518 A1 | 6/2003 | Dutta ......................... 623/1.38 |
| 2003/0113439 A1 | 6/2003 | Pacetti et al. .............. 427/2.24 |
| 2003/0150380 A1 | 8/2003 | Yoe ............................ 118/423 |
| 2003/0157241 A1 | 8/2003 | Hossainy et al. ........... 427/2.24 |
| 2003/0158517 A1 | 8/2003 | Kokish .................. 604/103.01 |
| 2003/0190406 A1 | 10/2003 | Hossainy et al. ........... 427/2.25 |
| 2003/0207020 A1 | 11/2003 | Villareal .................... 427/2.24 |
| 2003/0211230 A1 | 11/2003 | Pacetti et al. .............. 427/2.24 |
| 2004/0018296 A1 | 1/2004 | Castro et al. ............... 427/2.25 |
| 2004/0029952 A1 | 2/2004 | Chen et al. ................. 514/449 |
| 2004/0047978 A1 | 3/2004 | Hossainy et al. ............. 427/2.1 |
| 2004/0047980 A1 | 3/2004 | Pacetti et al. .............. 427/2.25 |
| 2004/0052858 A1 | 3/2004 | Wu et al. .................... 424/490 |
| 2004/0052859 A1 | 3/2004 | Wu et al. .................... 424/490 |
| 2004/0054104 A1 | 3/2004 | Pacetti ....................... 526/242 |
| 2004/0060508 A1 | 4/2004 | Pacetti et al. .............. 118/264 |
| 2004/0062853 A1 | 4/2004 | Pacetti et al. ............... 427/2.1 |
| 2004/0063805 A1 | 4/2004 | Pacetti et al. .............. 523/113 |
| 2004/0071861 A1 | 4/2004 | Mandrusov et al. ........ 427/2.24 |
| 2004/0072922 A1 | 4/2004 | Hossainy et al. ........... 523/113 |
| 2004/0073298 A1 | 4/2004 | Hossainy ................... 623/1.46 |
| 2004/0086542 A1 | 5/2004 | Hossainy et al. ........... 424/423 |
| 2004/0086550 A1 | 5/2004 | Roorda et al. .............. 424/448 |
| 2004/0096504 A1 | 5/2004 | Michal ....................... 424/471 |
| 2004/0098117 A1 | 5/2004 | Hossainy et al. ........... 623/1.42 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |

| | | |
|---|---|---|
| JP | 2001-190687 | 7/2001 |
| SO | 790725 | 2/1983 |
| SU | 872531 | 10/1981 |
| SU | 876663 | 10/1981 |
| SU | 905228 | 2/1982 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |
| WO | WO 00/74701 | 12/2000 |
| WO | WO 01/01890 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 04/009145 | 1/2004 |

OTHER PUBLICATIONS

U.S. Appl. No. 10/177,116, filed Jun. 21, 2002, Pacetti et al.
U.S. Appl. No. 10/177,114, filed Jun. 21, 2002, Simhambhatla et al.
U.S. Appl. No. 10/177,942, filed Jun. 21, 2002, Michal et al.
U.S. Appl. No. 10/176,506, filed Jun. 21, 2002, Claude et al.
U.S. Appl. No. 10/177,117, filed Jun. 21, 2002, Hossainy et al.
U.S. Appl. No. 10/320,899, filed Dec. 16, 2002, Shah et al.
Anonymous, Reducing the pH of a peptide oligomer to prepare for systemic delivery, Defensive Publication, Research Disclosure, p. 905 (Aug. 2003).
Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery of Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Biactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study and Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening space After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of a Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Anderson et al., *Nitric-Oxide and Nitrovasodilators: Similarities, Differences and Potential Interactions*, JACC 24(2):555-566 (1994).

Anderson et al., *Close Relation of Endothelial Function in the Human Coronary and Peripheral Circulations*, JACC 26(5):1235-1241 (1995).

Bode-Boger et al., *Elevated L-Arginine/Dimethylarginine Ratio Contributes to Enhanced Systemic NO Production by Dietary L-Arginine in Hypercholesterolemic Rabbits*, Biochem. And Biophys. Res. Comm. 219:598-603 (1996).

Bodmer et al., *Enhanced Recognition of a Modified Peptide Antigen by Cytotoxic T Cells Specific for Influenza Nucleoprotein*, Cell 52:253-258 (1988).

Boger et al., *An Endogenous Inhibitor of Nitric Oxide Synthase Regulates Endothelial Adhesiveness for Monocytes*, JACC 36(7):2287-2295 (2000).

Boger et al., *Asymmetric Dimethylarginine (ADMA):A Novel Risk Factor for Endothelial Dysfunction: Its Role in Hypercholesterolemia*, Circ. 98:1842-1847 (1998).

Boger et al., *Asymmetric Dimethylarginine: A Novel Risk Factor for Endothelial Dysfunction*, Circ. 96(8):I-32 (1997).

Boger et al., *The Endogenous NO Synthase Inhibitor Asymmetric Dimethyl-L-Arginine (ADMA) Regulates Endothelial NO Production and Adhesiveness for Monocytes* (Abstract J5), Nitric Oxide 2:126 (1998).

Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).

Candipan et al., *Dietary L-Arginine Attenuates Macrophage Infiltration and Intimal Hyperplasia After Balloon Injury* (Abstract 765-2), JACC 25:275A (1995).

Candipan et al., *Regression or Progression: Dependency on Vascular Nitric Oxide*, Arterioscler. Thromb. Vasc. Biol. 16(1):44-50 (1996).

Chan et al., *Asymmetric Dimethylarginine Increases Mononuclear Cell Adhesiveness in Hypercholesterolemic Humans*, Arterioscler. Thromb. Vasc. Biol. 20:1040-1046 (2002).

Cooke et al., *Arginine: A New Therapy for Atherosclerosis?* Circ. 95(2):311-312 (1997).

Cooke et al., *Cytoprotective Effects of Nitric Oxide*, Circ. 88(5)1:2451-2454 (1993).

Cooke et al., *Derangements of the Nitric Oxide Synthase Pathway, L-Arginine, and Cardiovascular Diseases*, Circ. 96(2):379-382 (1997).

Cooke et al., *Diffuse Coronary Artery Disease and Endothelial Dysfunction: Form Follows Function*, ACC Curr. J. Rev. pp. 19-25 (Nov./Dec. 2000).

Cooke et al., *Regression and Progression: Dependency Upon NO* (Abstract), J. Investi. Med. 43(2) Suppl. 2:211A (1995).

Cooke et al., *The Role of Endothelium-Derived Nitric Oxide in Atherosclerosis*, Adv. Vasc. Path. 1150:3-14 (1997).

Cooke, *Does ADMA Cause Endothelial Dysfunction?*, Arterioscler. Thromb. Vasc. Biol. 20:2032-2037 (2002).

Cooke, *Enhancement of Endogenous Vascular Nitric Oxide: A New Therapeutic Strategy for Restenosis* (Abstract 301), Eur. J. Clin. Investi. 28:A53 (1998).

Cooke, *Is Atherosclerosis and Arginine Deficiency Disease?*, J. Investi. Med. 46(8):377-380 (1998).

Cooke, *Nutriceuticals for Cardiovascular Health*, Am. J. Cardio., 82(10A):43S-46S (1998).

Cooke, *Role of Nitric Oxide in Progression and Regression of Atherosclerosis*, West. J. Med. 164(5):419-424 (1996).

Cooke, *The 1998 Nobel Prize in Medicine: Clinical Implications for 1999 and Beyond*, Vasc. Med. 4:57-60 (1999).

Cooke, *The Endothelium: A New Target for Therapy*, Vasc. Med. 5:49-43 (2000).

Cooke, *The Pathophysiology Of Peripheral Arterial Disease: Rational Targets for Drug Intervention*, Vasc. Med. 2:227-230 (1997).

Creager et al., *L-Arginine Improves Endothelium-Dependent Vasodilation in Hypercholesterolemic Humans*, J. Clin. Investi. 90:1248-1253 (1992).

Drexler et al., *Effect of L-Arginine on Coronary Endothelial Function in Cardiac Transplant Recipients: Relation to Vessel Wall Morphology*, Circ. 89(4):1615-1623 (1994).

Drexler et al., *Endothelial Dysfunction in the Coronary Circulation After Cardiac Transplantation: Effect of L-Arginine* (Abstract I356), Circ. 86(4) Supp:1418 (1992).

Dulak et al., *Nitric Oxide Induces the Synthesis of Vascular Endothelial Growth Factor by Rat Vascular Smooth Muscle Cells*, Arterioscler. Thromb. Vasc. Biol. 20:659-666 (2002).

http://www.If2.cuni.dz/physiolres/1997/issue5/iss5cl6.html, Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).

Gaiser et al., *Lethal Short-Limber Dwarfism in Transgenic Mice with an Arginine to Cysteine Substitution in Alpha-I (II) Procollagen* (Abstract 3369), Mol. Biol Cell 7:579A (1996).

Ganz et al., *Coronary Vasospasm in Humans—The Role of Atherosclerosis and of Impaired Endothelial Vasodilator Function*, Basic Res. Cardiol. 86(Suppl 2):215-222 (1991).

Gregory et al., *Enhanced Nitric Oxide Production Induced by the Administration of L-Arginine Does Not Inhibit Arterial Neointimal Formation After Overwhelming Alloimmune Injury*, J. Heart Lung Transplant. 15(1)Part 1:58-66 (1996).

Gregory et al., *Nitric Oxide Induced by the Administration of L-Arginine Does Not Inhibit Arterial Neointimal Formation Following Alloimmune Injury* (Abstract 41), J. Heart Lung Transplant. 14(1)Part 2:S45 (1995).

Heeschen et al., *Hypercholesterolemia Impairs Angiogenic Response to Hind Limb Ischemia: Role of ADMA* (Abstract 2490), Circ. I-473 (1999).

Ho et al., *Dietary L-Arginine Reverses the Inhibitory Effect of Asymmetric Dimethylarginine on Angiogenesis in Hypercholesterolemia* (Abstract 407-2), JACC 33:1A (1999).

Huet et al., *Structural Homologies Between Two HLA B27-Restricted Peptides Suggest Residues Important for Interaction with HLA B27*, Int. Immunol. 2(4):311-316 (1990).

Hutchison et al., *Effects of L-Arginine on Atherogenesis and Endothelial Dysfunction Due to Secondhand Smoke*, Hyperten. 34:44-50 (1999).

Jang et al., *Angiogenesis is Impaired by Hypercholesterolemia: Role of Asymmetric Dimethylarginine*, Circ. 102:1414-1419 (2000).

Jang et al., *L-Arginine Reverses the Anti-Angiogenic Effects of Asymmetric Dimethylarginine* (Abstract), J. Investi. Med. 4(2):86A (1999).

Jozkowicz et al., *Genetic Augmentation of Nitric Oxide Synthase Increases the Vascular Generation of VEGF*, Cardiovasc. Res. 51:773-783 (2001).

Kown et al., *Arginine Polymers Inhibit Graft Coronary Artery Disease Following Cardiac Transplantation* (Abstract 726), Transplant. 69(8):S300 (2000).

Kown et al., *L-Arginine Polymers Inhibit the Development of Vein Graft Neointimal Hyperplasia*, J. Thorac. Cardiovasc. Surg. 121(5):971-980 (2001).

Kown et al., *L-Arginine Polymer Mediated Inhibition of Graft Coronary: Artery Disease After Cardiac Transplantation*, Transplant. 71(11):1542-1548 (2001).

Krejcy et al., *Distribution and Metabolism of $N^G$-Nitro-L-Arginine and $N^G$-Nitro-L-Arginine Methylester in Canine Blood* in vitro, Naunyn-Schmiedeberg's Arch. of Pharmacol. 347(3):342-345 (1993).

Krejcy et al., *Metabolism of L-$N^G$-Nitro Arginine Methyl Ester in Human and Canine Plasma* (Abstract 207), J. Mol. Cell. Cardiol. 24(Supp IV):S108 (1992).

Kyte et al., *A Simple Method for Displaying the Hydropathic Character of a Protein*, J. Mol. Biol. 157:105-132 (1982).

Latron et al., *Positioning of a Peptide in the Cleft of HLA-A2 by Complementing Amino Acid Changes*, PNAS 88:11325-11329 (1991).

Lieberman et al., *Estrogen Improves Endothelium-Dependent, Flow-Mediated Vasodilation in Postmenopausal Women*, Annals Intern. Med. 121(12):936-941 (1994).

Lieberman et al., *Flow-Induced Vasodilation of the Human Brachial Artery is Impaired in Patients <40 Years of Age with Coronary Artery Disease*, Am. J. Cardiol. 78:1210-1214 (1996).

Lim et al., *Acute Local Delivery of L-Arginine Reduces Long Term Intimal Thickening and Macrophage Infiltration* (Abstract 2346), Circ. 94(8):I403 (1996).

Lin et al., *Addition of a Poly Arginine Linker to Cyclosporin A Facilitates Transcutaneous Delivery and Topical Inhibition of Cutaneous Inflammation* (Abstract 155), J. Inv. Derm. 114(4):777 (2000).

Lissin et al., *Maintaining the Endothelium: Prevention Strategies for Vessel Integrity*, Prev. Cardio. 3:172-177 (2000).

Maxwell et al., *A Medical Food Designed to Enhance Nitric Oxide Activity Restores Endothelium-Dependent Function in Hypercholesterolemia* (Abstract 140), Nitric Oxide: Biology and Chemistry 4(3):251(2000).

Maxwell et al., *A Nutritional Product Designed to Enhance Nitric Oxide Activity Restores Endothelium-Dependent Function in Hypercholesterolemia*, J. Investi. Med. 47(2):45A (1999).

Maxwell et al., *Cardiovascular Effects of L-Arginine*, Curr. Opin. Nephrol. Hyperten. 7:63-70 (1998).

Maxwell et al., *Endothelial Dysfunction in Hypercholesterolemia is Reversed by a Nutritional Product Designed to Enhance Nitric Oxide Activity*, Cardiovasc. Drugs Therapy 14:309-316 (2000).

Maxwell et al., *Improvement in Walking Distance and Quality of Life in Peripheral Arterial Disease by a Medical Food* (Abstract 86), Nitric Oxide: Biology and Chemistry, 4(3):232 (2000).

Maxwell et al., *Improvement in Walking Distance and Quality of Life in Peripheral Arterial Disease by a Nutritional Product Designed to Enhance Nitric Oxide Activity* (Abstract), J. Investi. Med. 47(2):63A (1999).

Maxwell et al., *L-Arginine Attenuates the Impairment in Exercise Capacity Due to Hypercholesterolemia* (Abstract), JACC 29:265A (1997).

Maxwell et al., *L-Arginine Enhances Aerobic Exercise Capacity in Association with Augmented Nitric Oxide Production*, J. Appl. Physiol. 90:933-938 (2001).

Maxwell et al., *Limb Blood Flow During Exercise is Dependent on Nitric Oxide*, Circ. 98:369-374 (1998).

Maxwell et al., *Modulation of the Nitric Oxide Synthase Pathway in Atherosclerosis*, Exp. Physiol. 83:573-584 (1998).

Maxwell et al., *Nutritional Therapy for Peripheral Arterial Disease: A Double-Blind, Placebo-Controlled, Randomized Trial of HeartBar®*, Vasc. Med. 5:11-19 (2000).

Maxwell et al., *The Role of Nitric Oxide in Atherosclerosis*, Cor. Art. Dis. 10:277-286 (1999).

Meredith et al., *Role of Endothelium in Ischemic Coronary Syndromes*, Am. J. Cardiol. 72(8):27C-32C (1993).

Meredith et al., *Role of Impaired Endothelium-Dependent Vasodilation in Ischemic Manifestations of Coronary Artery Disease*, Circ. 87(5) Suppl:V56-V66 (1993).

Mitchell et al.; *Polyarginine Enters Cells More Efficiently than Other Polycationic Homopolymers*, J. Peptide Res. 56:318-325 (2000).

Miyazaki et al., *Endogenous Nitric Oxide Synthase Inhibitor: A Novel Marker of Atherosclerosis*, Circ. 99:1141-1146 (1999).

http://pysiology.cup.cam.ac.uk/Proceedings/Abstracts/523P/Birmingham/Files/S32.html, Musialek et al., *The Nitric Oxide Donor Sodium Nitroprusside Increases Heart Rate In The Absence Of Changes In Arterial Blood Pressure When Applied Topically To The Sino-Atrial Node In The Anaesthetized Pig*, J. Physiol. (2000), printed Jun. 12, 2001.

Niebauer et al., *Effects of Chronic Exercise in Patients with Chronic Heart Failure on Markers of Oxidative Stress* (Abstract 1019-10), JACC 33:172A (1999).

Niebauer et al., *Endothelium-Derived Nitric Oxide Attenuates Monocyte-Endothelial Interaction in Chronic Hypercholesterolemia* (Abstract 2014) Circ. 92(8)Suppl I:I-422 (1995).

Niebauer et al., *Endotoxin and Immune Activation in Chronic Heart Failure: A Prospective Cohort Study*, Lancet 353:1838-1842 (1999).

Niebauer et al., *Gene Transfer of Nitric Oxide Synthase Effects on Endothelial Biology*, JACC 34(4):1201-1207 (1999).

Niebauer et al., *Local Delivery of L-Arginine After Balloon Angioplasty Time Course of Intramural L-Arginine Activity, Nitric Oxide Production and Monocyte Binding* (Abstract 3082), Circ. 96:I-551 (1997).

Niebauer et al., *Local L-Arginine Delivery After Ballon Angioplasty Reduces Monocyte Binding and Induces Apoptosis*, Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Ohno et al., *Shear Stress Elevates Endothelial cGMP: Role of a Potassium Channel and G Protein Coupling*, Circ. 88:193-197 (1993).

Raby et al., *Changing Vasomotor Responses of Coronary Arteries to Nifedipine*, Am. Heart J. 126(2):333-338 (1993).

Rothbard et al., *Conjugation of Arginine Oligomers to Cyclosporin A Facilitates Topical Delivery and Inhibition of Inflammation*, Nature Med. 6(11):1253-1257 (2000).

Rothbard et al., *Molecular Transporters Facilitate Topical Protein Transduction Into the Skin* (Abstract 957), J. Investi. Derm. 117(2):549 (2001).

Rothbard et al., *Reversal of HLA Restriction by a Point Mutation in an Antigenic Peptide*, Intl. Immunol. 1(4):487-495 (1989).

Safai et al., *L-Arginine/Nitric Oxide Pathway and Glomerular Injury in Preeclampsia* (Abstract A0504), J. Am. Soc. Nephrol. 9:98A (1998).

Schoolnik et al., *Gonococcal Pili: Primary Structure and Receptor Binding Domain*, J. Exp. Med. 159:1351-1370 (1984).

Schwarzacher et al., *L-$N^G$-Nitro-Arginine Methyl Ester in the Anesthetized Rabbit: Venous Vasomotion and Plasma Levels*, J. Vasc. Res. 29(3):290-292.

Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).

Schwarzacher et al., *Assessment of Changes in Vasomotor Tone in vivo Using Intravascular Ultrasound*, J. Pharmacol, Toxicol. Meth. 28(3):143-147 (1992).

Schwarzacher et al., *Blockade of Endothelium-Derived Relaxing Factor Synthesis with $N^G$-Nitro-L-Arginine Methyl Ester Leads of Enhanced Venous Reactivity in vivo*, Eur. J. Pharmacol. 229(2/3):253-258 (1992).

Schwarzacher et al., *Local Delivery of L-Arginine Increases Vascular Nitric Oxide Production and Improves Endothelium-Dependent Vasomotion* (Abstract P492), Eur. Heart J. 17:82 (1996).

Schwarzacher et al., *Local Delivery of L-Arginine Increases Vascular Nitric Oxide Production and Improves Endothelium Dependent Vasomotion* (Abstract 779-6), JACC 27(2) Supp IA:288A (1996).

Schwarzacher et al., *Local Intramural Delivery of L-Arginine Enhances Nitric Oxide Generation and Inhibits Lesion Formation After Balloon Angioplasty*, Circ. 95(7):1863-1869 (1997).

Schwarzacher, *New Therapeutic Approaches for Correction of Endothelial Function After Balloon Dilatation* (Eng. Abstract), J Kardiologie 7(1):14-17 (2000).

Schwarzacher et al., Altered Reactivity of the Inferior Vena Cava to Noradrenaline and Acetylcholine Following the Blockade of EDRF-Biosynthesis with $N^G$-Nitro-$_L$-Arginine Methyl Ester, Clin. Exp. Pharmacol. Physiol. 23(6/7):490-492.

Selwyn et al., *Pathophysiology of Ischemia in Patients with Coronary Artery Disease*, Prog. Cardiovasc. Dis. XXXV(1):27-39 (1992).

http://www.pharmsci.org/scientificjournals/pharmsci/journal/99_7.html, Shameem et al., *A Short Term (Accelerated Release) Approach to Evaluate Peptide Release from PLGA Depot-Formulations*, Published Jul. 21, 1999, printed Feb. 19, 2002.

Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).

Singer et al., *Anti-Atherogenic Effect of the EDRF Precursor* (Abstract I20), Circ. 86(4) Suppl:78 (1992).

Singer et al., *Chronic Supplementation with L-Arginine, the Precursor of Endogenous Nitric Oxide, Causes Tolerance to Nitroglycerin*, Circ. 86(4) Suppl:1942 (1992).

Singer et al., *Dietary Supplements of L-Arginine Reduce Atherogenesis and Aler Vascular Reactivity in Hypercholesterolemic Animals* (Abstract) Clin. Res. 41(1):78A (1993).

Singer et al., *Discordant Effects of Dietary L-Arginine on Vascular Structure and Reactivity in Hypercholesterolemic Rabbits*, J. Cardiovasc. Pharmacol. 25:710-716 (1995).

Stuehlinger et al., *Homocysteine Induced Accumulation of Asymmetric Dimethylarginine—Role of DDAH and Effect of Antioxidants* (Abstract 854), Circ. 102:II-177 (2000).

Suzuki et al., *Can Local Delivery of L-Arginine Reduce In-Stent Restenosis in Humans? An Ultrasound Volumetric Analysis* (Abstract 2459), Cir. 100(18) Suppl. I:I466-I467 (1999).

Tangphao et al., *Diurnal Variation of Plasma L-Arginine Concentrations and The Effect of Dietary L-Arginine Intake* (Abstract PII-25), Clin. Pharmacol. Therapeu. 63:178 (1998).

Tangphao et al., *L-Arginine and Nitric Oxide-Related Compounds in Plasma: Comparison of Normal and Arginine-Free Diets in a 24-h Crossover Study*, Vasc. Med. 4:27-32 (1999).

Theilmeier et al., *Adhesiveness of Mononuclear Cells in Hypercholesterolemic Humans is Normalized by Dietary L-Arginine*, Arterioscler. Thromb. Vasc. Biol. 17(12):3557-3564 (1997).

Theilmeier et al., *Adhesiveness of Mononuclear Cells is Increased in Hypercholesterolemic Humans, and Reduced by The NO Precursor* (Abstract 765-4), JACC 25:276A (1995).

Todd et al., *Regulation of Loblolly Pine (Pinus teada L.) Arginase in Developing Seedling Tissue During Germination and Post-Germinative Growth*, Plant Mol. Biol. 45:555-565 (2001).

Tsao et al., *Anti-Platelet Effect of Dietary L-Arginine, the Nitric Oxide Precursor* (Abstract 732-6), JACC 21(2):Suppl A:125A (1993).

Tsao et al., *Dietary Arginine Alters Endothelial Adhesiveness via NO* (Abstract), Clin. Res. 42(2):175A (1994).

Tsao et al., *Dietary L-Arginine Reduces Platelet Reactivity in Hypercholesterolemic Rabbits* (Abstract), Clin. Res. 41(1):78A (1993).

Tsao et al., *Endothelial Alterations in Hypercholesterolemia: More Than Simply Vasodilator Dysfunction*, J. Cardiovasc. Pharmacol. 32(Suppl 3):S48-S53 (1998).

Tsao et al., *Enhanced Endothelial Adhesiveness in Hypercholesterolemia is Attenuated by L-Arginine*, Circ. 89:2176-2182 (1994).

Tsao et al., *Exposure to Shear Stress Alters Endothelial Adhesiveness: Role of Nitric Oxide*, Circ. 92(12):3513-3519 (1995).

Tsao et al., *Fluid Flow Inhibits Endothelial Adhesiveness: Nitric Oxide and Transcriptional Regulation of VCAM-1*, Circ. 94(7):1682-1689 (1996).

Tsao et al., *L-Arginine Attenuates Platelet Reactivity in Hypercholesterolemic Rabbits*, Arterioscler. Thromb. 14(10):1529-1533 (1994).

Tsao et al., *Nitric Oxide Regulates Monocyte Chemotactic Protein-1*, Circ. 96(3):934-940 (1997).

Uemura et al., *Rapid and Efficient Vascular Transport of Arginine Polymers Inhibits Myointimal Hyperplasia*, Circ. 102:2629-2635 (2000).

Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).

Uemura et al., *Short Polymers of Arginine Rapidly Translocate into Vascular Cells: Effect on Nitric Oxide Synthesis* (Abstract 64), Circ. 102(18) Suppl II:II-16 (2000).

Vita et al., *Patients with Evidence of Coronary Endothelial Dysfunction as Assessed by Acetylcholine Infusion Demonstrate Marked Increase in Sensitivity to Constrictor Effects of Catecholamines*, Circ. 85(4):1390-1397 (1992).

von der Leyen et al., *Gene Therapy Inhibiting Neointimal Vascular Lesion: in vivo Transfer of Endothelial Cell Nitric Oxide Synthase Gene*, PNAS 92:1137-1141 (1995).

von der Leyen et al., *Overexpression of Constitutive, Endothelial-Type Nitric Oxide Synthase As an in vivo Gene Transfer Approach to Prevent Neointima Formation After Vascular Injury*, Clin. Res. 42(2):180A (1994).

Walls et al., *Effects of Growth Factors and L-Arginine on Ischemic Skin Flaps in Rats*, Vet. Surg. 24:484-491 (1995).

Wang et al., *Arginine Prevents Atherogenesis in the Coronary Artery of the Hypercholesterolemic Rabbit* (Abstract 732-2), JACC 21(2) Suppl A:124A (1993).

Wang et al., *Arginine Restores Nitric Oxide Activity and Inhibits Monocyte Accumulation After Vascular Injury in Hypercholesterolemic Rabbits*, JACC 28(6):1573-1579 (1996).

Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product.html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine In Cardiovascular Health*, U.S. Pharmacist Continuing Education, printed Sep. 12, 2002.

* cited by examiner

COATINGS FOR IMPLANTABLE MEDICAL DEVICES INCORPORATING CHEMICALLY-BOUND POLYMERS AND OLIGOMERS OF L-ARGININE

BACKGROUND OF THE INVENTION

1. Field of the Invention

This invention relates to the field of implantable medical devices, such as stents. More particularly, this invention is directed to coatings for devices, which include chemically bound polymers and/or oligomers of L-arginine.

2. Description of the Background

In the field of medical technology, there is frequently a necessity to administer a therapeutic substance locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results. For the treatment of vascular occlusions, such as restenosis, stents are being modified to administer therapeutic substances locally. One method of medicating a stent is with the use of a polymer coating impregnated with a therapeutic substance. The coating allows for the sustained release of the substance at the treatment site. L-arginine, or polypeptide oligomeric derivatives or analogs thereof, for example, those containing 5 to 20 amino acid units are one example of a therapeutic substance that can be used in conjunction with a stent.

L-arginine is a known precursor of endothelium derived nitric oxide (NO). NO is synthesized from L-arginine, or its polymeric and/or oligomeric derivatives, by the enzyme NO synthase, a homodimeric flavo-hemoprotein that catalyzes the 5-electron oxidation of L-arginine to produce NO and L-citrulline. Among other therapeutic properties, NO relaxes vascular smooth muscle cells and inhibits the cells' proliferation. Inhibition of proliferation of vascular smooth muscle cells is believed to contribute to the reduction or elimination of restenosis.

U.S. Pat. No. 5,861,168 to Cooke et al. teach that NO activity is reduced after vascular injury. Cooke et al. also teach that administering L-arginine as the NO precursor helps to restore vascular NO activity in patients with endothelial vasodilator dysfunction due to restenosis.

However, introducing L-arginine into a stent coating by mere mechanical or physical blending with a polymer may be insufficient to achieve maximum therapeutic results. In other words, L-arginine will have a tendency to be released quickly when the stent coating is brought into contact with body fluids such as blood. The short residence time of the compound may be insufficient for the effective treatment of the patient. Accordingly, increasing the residence time of L-arginine at the implantation site is desired.

In addition, the amount of NO generated by L-arginine, or its polymers and/or oligomers, may be insufficient to achieve the best therapeutic results. Consequently, it is desirable to obtain an additional amount of NO upon decomposition of L-arginine, or its polymers and/or oligomers, caused by NO synthase oxygenase enzyme. Accordingly, it is desirable to incorporate an additional source of NO into the molecule of L-arginine, or its polymers and/or oligomers.

SUMMARY

In accordance with one embodiment of the invention, a coating for an implantable medical device, such as a stent, is provided. The coating comprises a polymer and an amino acid chemically bonded, attached or conjugated to the polymer. The amino acid includes polymers and/or oligomers of L-arginine, and copolymers of L-arginine with lysine. The oligomers of L-arginine can be a heptamer or a nonamer. The polymer can have at least one reactive group, for example, a hydroxyl, a carboxyl, or a glycidyl group. Representative examples of polymers include poly(ethylene-co-vinyl alcohol), poly(butyl methacrylate-co-2-hydroxyethyl methacrylate), poly(ethylene glycol), poly(ethylene-co-acrylic acid), poly(ethylene-co-glycidyl methacrylate), and mixtures thereof. In one embodiment, a therapeutic substance can be dispersed in the polymer for inhibiting or eliminating restenosis of a blood vessel. In another embodiment, a nitric oxide donor can be chemically conjugated to the amino acid. The nitric oxide donor can comprise a diazenium diolate type nitric oxide donor, wherein the diazenium diolate type donor can be spermine diazenium diolate, 1-{N-methyl-N-[6-(N-methylammonio) hexyl]amino} diazen-1-ium-1,2-diolate, Z-1-[N-(2-aminoethyl)-N-(2-ammonioethyl)amino]diazen-1-ium-1,2-diolate and mixtures thereof.

In accordance with another embodiment of the invention, a coating for an implantable medical device, such as a stent, is provided. The coating comprises a polymer; a therapeutic substance contained by the polymer for the sustained release of the therapeutic substance; and, an amino acid chemically bonded, attached or conjugated to the polymer, the therapeutic substance, or both. The therapeutic substance can be, for example, rapamycin or analogs or derivatives thereof, taxol or analogs or derivatives thereof, or anti-sense oligonucleotides.

In accordance with another embodiment of the invention a method of coating an implantable medical device, such as a stent, is provided. The method comprises forming a coating on the device, the coating comprising a polymer and an amino acid chemically bonded or conjugated to the polymer.

DETAILED DESCRIPTION

L-arginine, commonly abbreviated as "R" or "Arg," is an amino acid having a formula $NH=C(NH_2-NH-CH_2-CH_2-CH_2-CH(NH_2)-COOH$. L-arginine is also known as 2-amino-5-guanidinovaleric acid. Polymers and/or oligomers of L-arginine that can be used are herein referred to as "PArg" and comprise a plurality of repeating monomeric amino acid units connected with peptide bonds. The PArg polymers and/or oligomers have a general formula $H[NH-CHX-CO]_p-OH$, where "p" can be within a range of 5 and 1,000, such as for example, within a range of between 5 and 20. In one embodiment, a heptamer (designated R7) or a nonamer (R9), having p=7 and p=9, respectively, can be used. In the formula of PArg, "X" is a 1-guanidinopropyl radical having the structure $-CH_2-CH_2-NH_2-NH-C(NH_2)=NH$. The terms "polymers and/or oligomers of L-arginine," and "PArg" are intended to include L-arginine in both its polymeric and oligomeric form.

The family of polymers that can be used to make coatings for medical devices according to the embodiments of the present invention can be characterized by the presence of a polyolefin backbone, pendant on which are reactive groups, for example hydroxyl, glycidyl, carboxyl, and/or other suitable reactive groups. PArg, such as R7 or R9 can be chemically bonded or attached to the polymer's backbone utilizing one or more of the pendant reactive groups, for example the hydroxyl groups. A copolymer of ethylene and vinyl alcohol (EVOH) is one example of a polymer on which PArg, such as R7 or R9, can be chemically grafted. Poly (ethylene-co-vinyl alcohol) is also known under the trade name EVAL and is distributed commercially by Aldrich Chemical Company of Milwaukee, Wis. EVAL is also manufactured by EVAL Company of America of Lisle, Ill. EVAL has the general formula $—[CH_2—CH_2]_m—[CH_2—CH(OH)]_n—$. EVAL is a product of hydrolysis of ethylene-vinyl acetate copolymers. EVAL may also be a terpolymer and may include up to 5% (molar) of units derived from styrene, propylene and other suitable unsaturated monomers.

Other representative examples of polymers include, but are not limited to, poly(butylmethacrylate-co-2-hydroxyethyl methacrylate) (p(BMA-HEMA)), poly(butylmethacrylate)-co-poly(2-hydroxyethyl methacrylate) (PBMA-PHEMA), poly(ethylene glycol) (PEG), poly(ethylene-co-acrylic acid)(PEAA), poly(ethylene-co-glycidyl methacrylate)(PEGMA), EVAL-PEG blends, and other mixtures and combinations thereof.

PArg can be chemically bonded to one or a blend of polymers by covalent conjugation of the PArg to the polymer. The functional groups of the polymers, such as the hydroxyl groups in EVAL, PEG or PHEMA, the carboxyl groups in PEAA, or the glycidyl groups in PEGMA, are used as sites for the conjugation. The grafting of PArg to the polymer can be conducted directly on the stent or the grafting to the polymer can be performed first, and the product is then applied on the stent to form a coating.

In accordance with another embodiment, instead of PArg, a copolymer of L-arginine with another amino acid can be chemically bonded the polymer or combination of polymers. One example of an amino acid that can be combined with L-arginine by co-polycondensation is L-lysine, also known as 2,6-diaminohexanoic acid, having the formula $NH_2—(CH_2)_4—CH(NH_2)—COOH$.

A co-peptide of L-arginine and L-lysine can be prepared using standard methods of peptide synthesis known to those having ordinary skill in the art. If L-lysine is used, in the L-arginine-L-lysine co-peptide, the molar ratio between the units derived from L-lysine and L-arginine can be, for example, about 1:7; that is, for about every 7 L-arginine-derived units, there appears 1 L-lysine-derived unit.

In accordance with another embodiment, an additional source of NO can be chemically incorporated into PArg. This is achieved by modifying PArg with a molecule-source of NO, followed by grafting of the modified PArg to the backbone of the polymer. Alternatively, unmodified PArg can be first grafted to the polymer, followed by reacting with the molecule-source of NO. Sources of additional NO include diazenium diolate type nitric oxide donors, which are adducts of nitric oxide with nucleophilic amines. Diazenium diolates, also known as "NONOates," are highly biologically compatible, and in slightly acidic medium they spontaneously release NO. One example of diazenium diolate that can be used is spermine diazenium diolate (SDD).

An aliphatic NONOate, SDD, or 1,3-propanediamine, N-{4-[1-(3-aminopropyl)-2-hydroxy-2-nitrosohydrazino] butyl}-diazen-1-ium-1,2-diolate has the formula $NH_2(CH_2)_3—N[N^+(O)—(N^-—OH)]—(CH_2)_4—NH—(CH_2)_3—NH_2$ and is manufactured by Molecular Probes, Inc. of Eugene, Oreg. Alternatively, other diazenium diolate-type NO donors can be used. Examples of such alternative diazenium diolate-type NO donors include such compounds as, for instance, 1-{N-methyl-N-[6-(N-methylammonio) hexyl]amino}diazen-1-ium-1,2-diolate having the formula $CH_3—N^+H_2—(CH_2)_6—N(CH_3)—N^+(O^-)\!=\!N—O^-$ (MAHMA-NO), or Z-1-[N-(2-Aminoethyl)-N-(2-ammonioethyl)amino]diazen-1-ium-1,2-diolate having the formula $O—N^+[N(CH_2CH_2NH_2)CH_2CH_2N^+H_3]\!=\!N—O^-$ (DETA-NO). MAHMA-NO and DETA-NO can be obtained from Cayman Chemical Co. of Ann Arbor, Mich.

In accordance with another embodiment of the invention, a therapeutic substance or a drug can be incorporated into the polymeric coating. The therapeutic substance can include any substance capable of exerting a therapeutic or prophylactic effect for the patient. For example, the therapeutic substance can be for inhibit the activity of vascular smooth muscle cells. The substance can be directed at inhibiting abnormal or inappropriate migration and/or proliferation of smooth muscle cells to inhibit restenosis. The drug may include small molecule drugs, peptides, proteins, oligonucleotides, or double-stranded DNA.

Examples of therapeutic substances include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The substance can also fall under the genus of antineoplastic, anti-inflammatory, antiplatelet, anticoagulant, antifibrin, antithrombin, antimitotic, antibiotic, antiallergic and antioxidant substances. Examples of antineoplastics and/or antimitotics include paclitaxel, docetaxel, methotrexate, azathioprine, vincristine, vinblastine, fluorouracil, doxorubicin hydrochloride, and mitomycin.

Examples of antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3- fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon genetically engineered epithelial, endothelial, vascular smooth muscle cells, or other cells; cell cycle inhibitors such as rapamycin and its derivatives and analogs, and flavopiridol; the estrogen receptors such as estrogen, estrogen analogs, tamoxifen, and idoxifene; the retinoid receptors, such as retinal and retinoic acid; the PPAR alpha and gamma receptors such as troglitizone, rosiglitazone and pioglitazone; inhibitors of cell signaling including inhibitors of Ras and the MAP kinase cascade; inhibitors of receptor tyrosine kinases; steroid receptors such as clobetasol, dexamethasone, and derivatives or analogs thereof.

In accordance with yet another embodiment, PArg can be conjugated to the therapeutic substance, in addition to, or instead of, being conjugated to the polymer. For example, PArg can be chemically bonded or attached to rapamycin, or derivatives or analogs thereof, taxol and anti-sense oligonucleotides.

The polymer can be used to form a coating for a balloon expandable or self-expandable stent. The use of the coating is, however, not limited to stents and the coating can also be used with a variety of other medical devices. Examples of an implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the present invention are further illustrated by the following examples.

EXAMPLE 1

R7 can be grafted to EVAL. Optionally, an NO donor, such as DETA-NO can be first conjugated to R7. EVAL with m:n ratio of 44:56 can be used. EVAL with a higher or lower ethylene content can be modified by the same methods as those discussed below. The first optional step of grafting includes conjugation of DETA-NO to R7 utilizing an amide linkage with R7 according to the following reaction scheme (I):

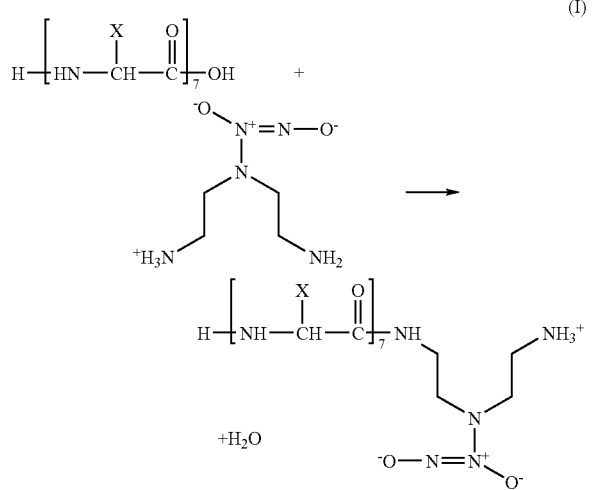

A variation of reaction (I) includes cross-linking of R7 with DETA-NO using a imidoester cross-linking agent, such as dimethyl adipimidate (DMA), dimethyl pimelimidate (DMP) or dimethyl 3,3'-dithiobispropionimidate (DTBP). DMA, DMP and DTBP are manufactured commercially by Pierce Corp. of Rockford, Ill.

Next, EVAL can be halogenated by phosphorous trichloride $PCl_3$, phosphorous pentachloride $PCl_5$ thionyl chloride $SOCl_2$, or other appropriate halogenating agent, via EVAL's hydroxyl group. This process, a nucleophilic substitution $S_N2$ can be schematically illustrated according to reaction (II):

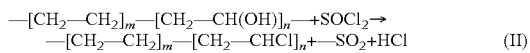

$$—[CH_2—CH_2]_m—[CH_2—CH(OH)]_n—+SOCl_2 \rightarrow$$
$$—[CH_2—CH_2]_m—[CH_2—CHCl]_n—+SO_2+HCl \quad (II)$$

Next, the non-protonated non-terminal primary amino groups of R7 are protected by reaction (III) with 9-fluorenylmethyl chloroformate in aqueous dioxane, where 9-fluorenylmethyl chloroformate, also known as 9-fluorenylmethyloxycarbonylchloride or FMOC-chloride, has the formula

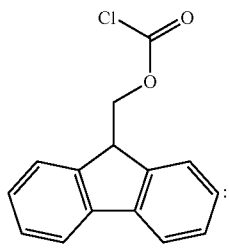

and, reaction (III) is

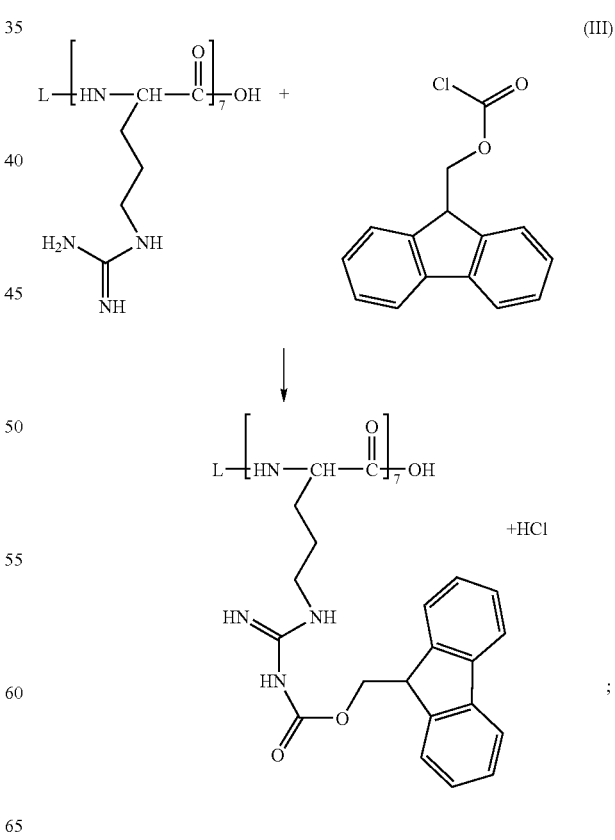

where L is either H (if the optional grafting of DETA-NO shown in reaction (I) was not performed) or DETA-NO.

The reaction of esterification (IV) is carried out where the carboxyl group of the protected R7 is reacted with the halogenated EVAL obtained in reaction (II):

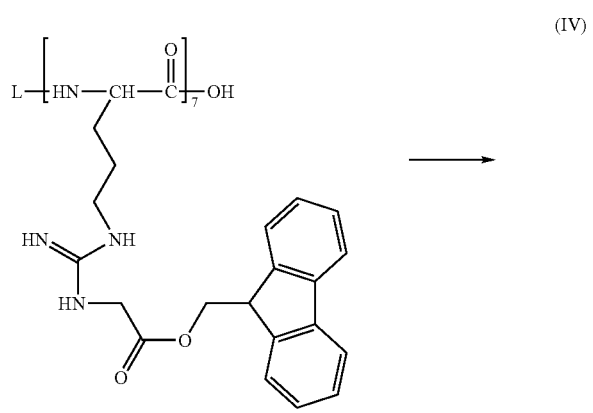

Finally, the product of reaction (IV) is cleaved by 50% morpholine or other appropriate amine.

As a result of the nucleophilic reaction (IV), R7 (with or without the additional source of NO) is bound or attached to EVAL by a labile ester bond. This bond is hydrolytically weak and will be broken when the stent is subjected to the body fluids. Thus, R7 will be released bringing about a desirable therapeutic effect. The reactions schemes described above are conducted under standard conditions which are known to those having ordinary skill in the art.

EXAMPLE 2

DETA-NO can be optionally grafted to R7 as shown in Example 1, reaction (I). Next, the non-protonated, non-terminal primary amino groups of R7 are protected by reaction with 9-fluorenylmethyl chloroformate in aqueous dioxane as shown in Example 1, reaction (III).

The reaction of direct esterification is then carried out, as a result of which, the carboxyl group of R7 is conjugated to EVAL in the presence of 1,3-dicyclohexylcarbodiimide (DCC) having the formula

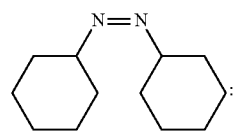

wherein, DCC activates the carboxyl group of R7, thus facilitating the esterification reaction of nucleophilic substitution (V):

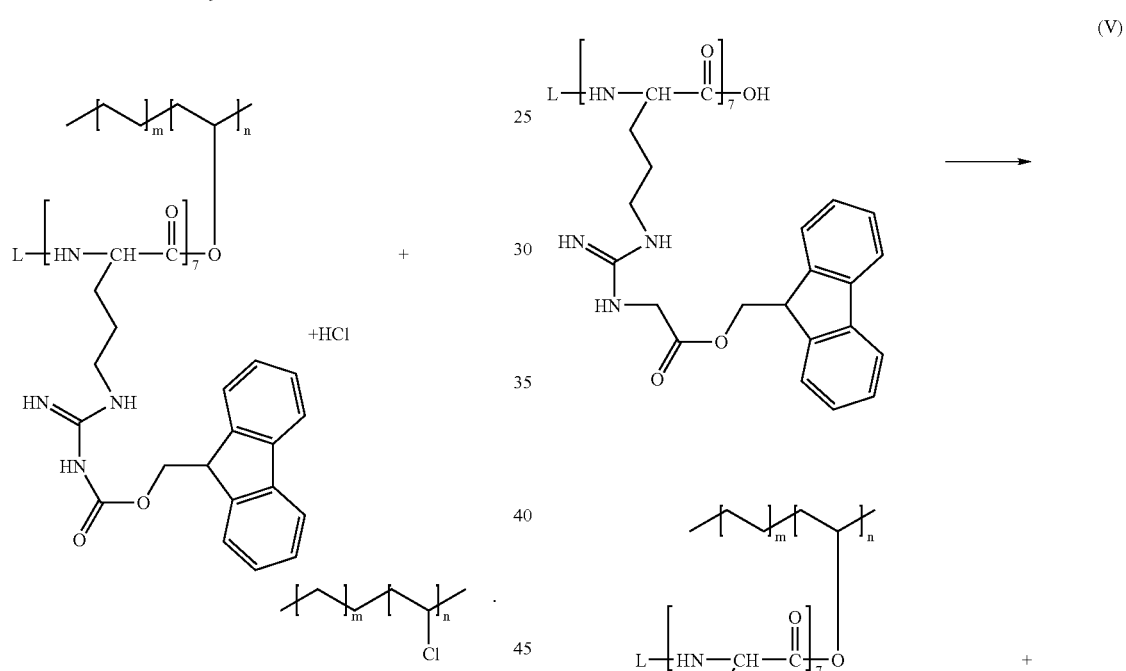

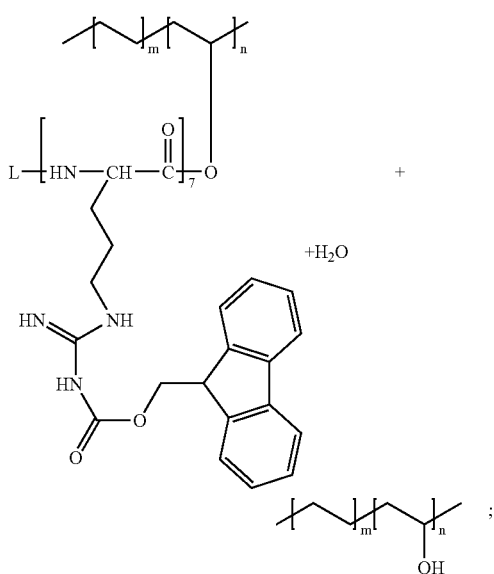

where L is defined in Example 1.

Reaction (V) is conducted under standard conditions known to those having ordinary skill in the art. An insoluble substance, N,N-dicyclohexylurea, having the formula

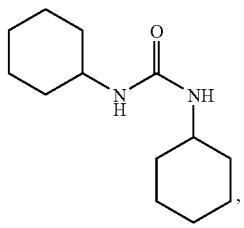

is a by-product of the reaction (V). Finally, the R7-EVAL conjugate, the product of reaction (V), is de-protected by a reaction with morpholine or another appropriate amine, as in Example 1.

Alternatively, the reaction of direct esterification can be carried out in the presence of dimethylaminopyridine (DMAP).

As a result of the reaction (V), R7 (with or without the additional source of NO) is bound or attached to EVAL by a labile ester bond.

EXAMPLE 3

The preparation of EVAL-R7 conjugate is similar to Example 1, but the order of steps can be different. First, the non-protonated, non-terminal primary amino groups of R7 are protected by reaction with 9-fluorenylmethyl chloroformate in aqueous dioxane as shown in Example 1, reaction (III). Next, EVAL is reacted with the protected R7. This can be accomplished using preliminarily halogenated EVAL as shown by reaction (IV), Example 1. Alternatively, a direct esterification in the presence of DCC or DMAP can be used as in Example 2.

Next, DETA-NO can be optionally grafted to R7 as shown in Example 1, reaction (I). Instead of DMA, DMP or DTBP, discussed in Example 1, a di-succinimidyl ester in a non-aqueous solvent (e.g., dimethyl acetoamide) can be used at a temperature of about 40° C. in a slightly basic medium (e.g., pH~7.4) to perform the cross-linking of DETA-NO with R7. Examples of suitable di-succinimidyl esters include bis(succinimidooxycarbonyloxyethyl sulfone) (BSOCOES) having the formula [M—O—C(O)—O—$CH_2$—$CH_2$]$_2$—$SO_2$, and dithiobis(succinimidyl propionate) (DTSP) having the formula [M—O—C(O)O—$CH_2$—$CH_2$—S—]$_2$. In both BSOCOE and DTSP, M is a succinimide group. BSOSOES and DTSP can be obtained from Molecular Biosciences, Inc. of Boulder, Colo. DTSP is also known as the Lomant's reagent.

Finally, the R7-EVAL conjugate, the product of the above-described process, is de-protected by a reaction with morpholine or another appropriate amine, as in Example 1.

As a result, R7 (with or without the additional source of NO) is bound or attached to EVAL by a labile ester bond.

EXAMPLE 4

EVAL can be preliminarily derivatized by tosylation (treatment with tosyl chloride), or alternatively by tresylation (by reacting with tresyl chloride). Tosyl chloride is a derivative of toluene, para-toluenesulfonil chloride having the formula $CH_3$—$C_6H_4$—$SO_2Cl$ (TsCl). The process of EVAL derivatization can be conducted directly on the stent. The following process of tosylation can be used.

A 2% (mass) solution of EVAL in dimethylacetamide (DMAC) can be sprayed on the stent and dried for 10 minutes at 80° C., and then for 1 hour at 140° C. A 3% (mass) of TsCl in dry xylene can be prepared and the coated EVAL stent can be shaken for 1 minute with 1.4 ml of the TsCl solution. 0.25 ml of 33% (mass) of pyridine in dry xylene can be added, followed by shaking for 4 hours in desiccator. The stent can then be rinsed with acetone and twice with 1 mM solution of HCl to remove the excess TsCl.

As a result, EVAL is tosylated according to reaction (VI) and tosyl group is attached to the EVAL backbone via hydroxy group to yield the toluenesulfoester:

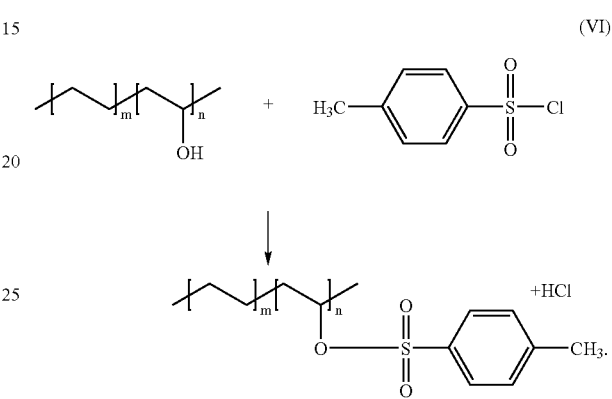

(VI)

Alternatively, tresyl chloride (2,2,2-trifluoroethanesulphonyl chloride) can be used to derivatize EVAL, according to reaction scheme (VII) and a tresyl group is attached to the EVAL backbone via hydroxy group:

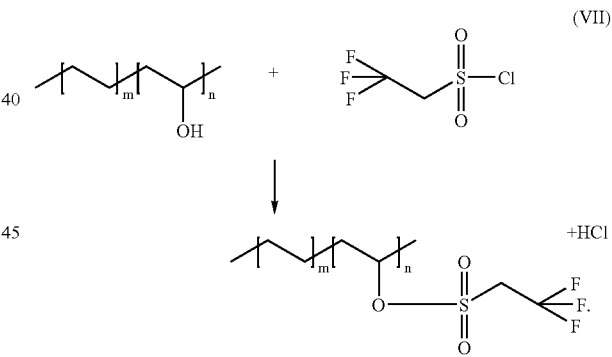

(VII)

Next, DETA-NO can be optionally grafted to R7 as shown in Example 1, reaction (I), followed by protecting the non-protonated, non-terminal primary amino groups of R7 by reaction with 9-fluorenylmethyl chloroformate in aqueous dioxane as shown in Example 1, reaction (III).

The protected R7 can then be added to the tosylated or tresylated EVAL, while the pH is maintained at a neutral or slightly basic level. The protected R7 is chemically quite active because its carboxyl group at pH≧7 is in the ionized (de-protonated) form, $COO^-$. Accordingly, the protected R7 under such conditions is a stronger nucleophile than the tosylated anion on EVAL and readily enters into a reaction of nucleophilic substitution with the tosylated or tresylated EVAL in solution.

In addition, since toluenesulfonic acid is known to be a very strong acid, on par with sulfuric or hydrochloric acids, its anion, $CH_3$—$C_6H_4$—$SO_3^-$, is an excellent leaving group in the nucleophilic substitution alkylation reaction between the protected R7 and EVAL, much better than the hydroxyl group of an underivatized EVAL.

Consequently, the tosylated EVAL obtained as described above, readily reacts with the protected R7 as schematically shown by the alkylation reaction (VIII):

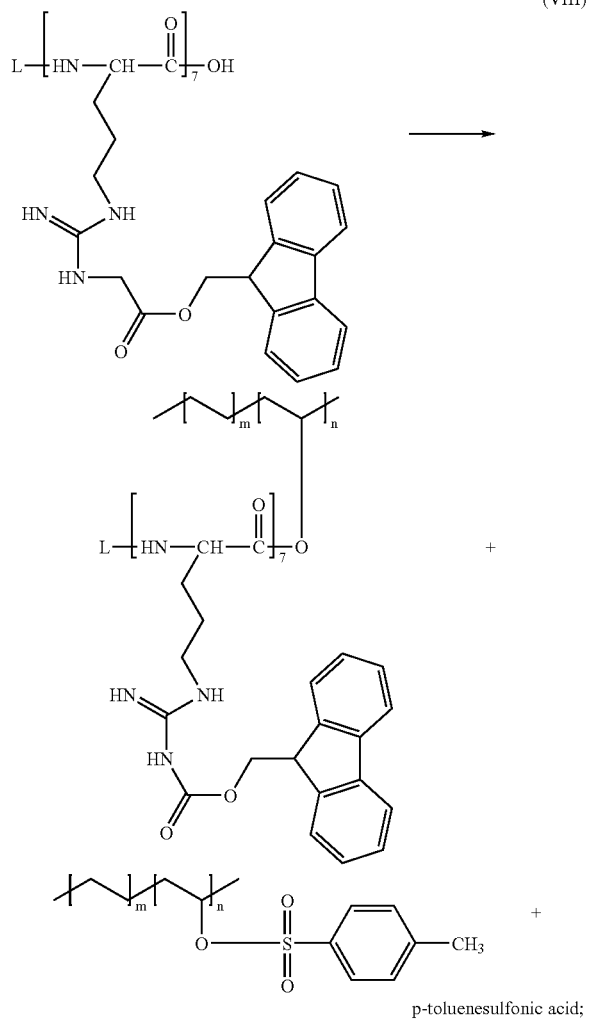

where L is defined in Example 1.

The conditions under which reaction (VIII) is conducted can be determined by those having ordinary skill in the art. The reaction of tresylated EVAL and the protected R7 is similar to reaction (VIII).

Finally, the R7-EVAL conjugate, the product of reaction (VIII), is de-protected by a reaction with morpholine or another appropriate amine, as in Example 1.

As a result of the reaction (VIII), R7 (with or without the additional source of NO) is bound or attached to EVAL by a labile ester bond.

EXAMPLE 5

DETA-NO can be optionally grafted to R7 as shown in Example 1, reaction (I), followed by protecting the non-protonated amino groups of R7 by reaction with 9-fluorenylmethyl chloroformate in aqueous dioxane as shown in Example 1, reaction (III). The protected R7 is then halogenated by thionyl chloride or phosphorous tri- or pentachloride. The reaction of halogenation is similar to reaction (II) shown in Example 1, except that instead of halogenating hydroxyl groups, here the terminal carboxyl groups of the protected R7 are halogenated.

The halogenated protected R7 is then esterified by reacting with EVAL to form labile ester bonds. This esterification reaction is a mirror image of reaction (IV) described in Example 1. Finally, the R7-EVAL conjugate, the product of this esterification reaction, is de-protected by a reaction with morpholine or another appropriate amine, as in Example 1.

As a result, R7 (with or without the additional source of NO) is bonded or attached to EVAL by a labile ester bond.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, the coating comprising a polymer and an amino acid chemically bonded to the polymer, wherein the amino acid comprises L-arginine.

2. The coating of claim 1, wherein the medical device comprises a stent.

3. A coating for an implantable medical device, the coating comprising a polymer and an amino acid chemically bonded to the polymer, wherein the amino acid comprises polymers and/or oligomers of L-arginine, or copolymers or co-peptides of L-arginine with lysine.

4. The coating of claim 3, wherein the oligomers of L-arginine include a heptamer or a nonamer.

5. The coating of claim 1, wherein the polymer has at least one reactive group.

6. The coating of claim 5, wherein the reactive group comprises a hydroxyl, a carboxyl or a glycidyl group.

7. The coating of claim 1, wherein the polymer comprises a component selected from a group consisting of poly (ethylene-co-vinyl alcohol), poly(butyl methacrylate-co-2-hydroxyethyl methacrylate), poly(ethylene glycol), poly (ethylene-co-acrylic acid), poly(ethylene-co-glycidyl methacrylate), and mixtures or combinations thereof.

8. The coating of claim 1, additionally including a therapeutic substance dispersed in the polymer effective for inhibiting or eliminating restenosis of a blood vessel.

9. The coating of claim 1, further comprising a nitric oxide donor chemically conjugated to the amino acid.

10. The coating of claim 9, wherein the nitric oxide donor comprises a diazenium diolate type nitric oxide donor.

11. The coating of claim 10, wherein the diazenium diolate type donor comprises a component selected from a group consisting of spermine diazenium diolate, 1-{N-methyl-N-[6-(N-methylammonio)hexyl]amino}diazen-1-ium-1,2-diolate, Z-1-[N-(2-aminoethyl)-N-(2-ammonioethyl) amino]diazen-1-ium-1,2-diolate and mixtures thereof.

12. A coating for an implantable medical device, the coating comprising a polymer, a therapeutic substance contained by the polymer for the sustained release of the therapeutic substance and an amino acid chemically bonded, attached or conjugated to the polymer, the therapeutic substance, or both, wherein the amino acid comprises L-arginine.

13. The coating of claim 12, wherein the therapeutic substance comprises antiproliferatives rapamycin or analogs or derivatives thereof, paclitaxel or analogs or derivatives thereof, docetaxel or analogs or derivatives thereof, or anti-sense oligonucleotides.

14. The coating of claim 12, wherein the implantable medical device comprises a stent.

15. A coating for an implantable medical device, the coating comprising a polymer, a therapeutic substance contained by the polymer for the sustained release of the therapeutic substance and an amino acid chemically bonded, attached or conjugated to the polymer, the therapeutic substance, or both, wherein the amino acid comprises polymers and/or oligomers of L-arginine, or copolymers or co-peptides of L-arginine with lysine.

16. The coating of claim 15, wherein the oligomers of L-arginine include a heptamer or a nonamer.

17. The coating of claim 12, wherein the polymer has at least one reactive group comprising a component selected from a group consisting of a hydroxyl, a carboxyl or a glycidyl group.

18. The coating of claim 12, further comprising a nitric oxide donor chemically conjugated to the amino acid.

19. The coating of claim 18, wherein the nitric oxide donor comprises a diazenium diolate type nitric oxide donor.

20. A method of coating an implantable medical device, comprising forming a coating on the device, the coating comprising a polymer and an amino acid chemically bonded, attached or conjugated to the polymer, wherein the amino acid comprises L-arginine.

21. The method of claim 20, wherein the medical device comprises a stent.

22. A method of coating an implantable medical device, comprising forming a coating on the device, the coating comprising a polymer and an amino acid chemically bonded attached or conjugated to the polymer, wherein the amino acid comprises polymers and/or oligomers of L-arginine, or copolymers or co-peptides of L-arginine with lysine.

23. The method of claim 22, wherein the oligomers of L-arginine include a heptamer or a nonamer.

24. The method of claim 20, additionally including a therapeutic substance dispersed in the polymer effective for inhibiting or eliminating restenosis of a blood vessel.

25. The method of claim 20, wherein the polymer has at least one reactive group.

26. The method of claim 25, wherein the reactive group comprises a component selected from a group consisting of a hydroxyl, a carboxyl or a glycidyl group.

* * * * *